US012667528B2

(12) United States Patent
Wu et al.

(10) Patent No.: US 12,667,528 B2
(45) Date of Patent: Jun. 30, 2026

(54) HIGH-TEMPERATURE-RESISTANT FRAGRANCE BEAD AND PREPARATION METHOD THEREFOR

(71) Applicant: FOSHAN MAGIC CRYSTAL TECHNOLOGY DEVELOPMENT CO., LTD., Foshan (CN)

(72) Inventors: Jiyuan Wu, Foshan (CN); Fengsheng Wang, Foshan (CN); Chiseng Wong, Foshan (CN)

(73) Assignee: FOSHAN MAGIC CRYSTAL TECHNOLOGY DEVELOPMENT CO., LTD., Foshan (CN)

( * ) Notice: Subject to any disclaimer, the term of this patent is extended or adjusted under 35 U.S.C. 154(b) by 0 days.

(21) Appl. No.: 18/727,538

(22) PCT Filed: Mar. 14, 2024

(86) PCT No.: PCT/CN2024/081766
§ 371 (c)(1),
(2) Date: Jul. 9, 2024

(87) PCT Pub. No.: WO2024/255358
PCT Pub. Date: Dec. 19, 2024

(65) Prior Publication Data
US 2025/0114284 A1 Apr. 10, 2025

(30) Foreign Application Priority Data
Oct. 10, 2023 (CN) .......................... 202311310054.3

(51) Int. Cl.
| | |
|---|---|
| *A61K 8/11* | (2006.01) |
| *A61K 8/73* | (2006.01) |
| *A61Q 13/00* | (2006.01) |

(52) U.S. Cl.
CPC ............... *A61K 8/11* (2013.01); *A61K 8/732* (2013.01); *A61Q 13/00* (2013.01)

(58) Field of Classification Search
CPC .......... A61K 8/11; A61K 8/732; A61Q 13/00
See application file for complete search history.

(56) References Cited

U.S. PATENT DOCUMENTS

| | | | | |
|---|---|---|---|---|
| 4,020,156 A | * | 4/1977 | Murray | ................... A61L 9/046 424/401 |
| 2007/0021515 A1 | * | 1/2007 | Glenn | ...................... C08J 9/125 521/99 |
| 2009/0142812 A1 | * | 6/2009 | Skuratowicz | ........... C12P 19/14 435/95 |
| 2011/0083680 A1 | * | 4/2011 | Mishra | ................. A24B 15/283 131/275 |
| 2015/0140181 A1 | | 5/2015 | Givaudan | |
| 2020/0216572 A1 | * | 7/2020 | Heinze | ................... C08B 30/12 |
| 2020/0345600 A1 | * | 11/2020 | Brady | .................... A61Q 19/10 |
| 2022/0295862 A1 | * | 9/2022 | Clark | ....................... A24B 3/14 |

FOREIGN PATENT DOCUMENTS

| | | |
|---|---|---|
| CN | 1843191 A | 10/2006 |
| CN | 112522040 A | 3/2021 |
| CN | 112920914 A | 6/2021 |
| CN | 113563987 A | 10/2021 |
| CN | 117265868 A | 12/2023 |
| EP | 0922449 A2 | 6/1999 |
| WO | 2023006648 A1 | 2/2023 |

OTHER PUBLICATIONS

Donald John Calvien Hutabarat and Jansen Stevensen. "Physicochemical Properties of Enzymatically Modified Starch: A Review." 2023 IOP Conf. Ser.: Earth Environ. Sci., 1169 012093, pp. 1-10. (Year: 2023).*

Guo et al. "Synergistic effects of branching enzyme and transglucosidase on the modification of potato starch granules." International Journal of Biological Macromolecules, 2019, 130: 499-507. (Year: 2019).*

Written Opinion issued on Apr. 17, 2024, in corresponding International Application No. PCT/CN2024/081766, 10 pages.

International Search Report issue on Apr. 17, 2024, in corresponding International Application No. PCT/CN2024/081766, 4 pages.

* cited by examiner

*Primary Examiner* — Doan T Phan

(74) *Attorney, Agent, or Firm* — Maier & Maier, PLLC

(57) ABSTRACT

A fragrance bead and a preparation method therefor, relating to the technical field of fragrance beads. A melting temperature of the fragrance bead is >50° C., modified starch is an encapsulating material, and an average molecular weight of the modified starch is 5,000 to 20,000. By using modified starch with a higher melting temperature as an encapsulating material, the melting temperature of the fragrance bead is increased to meet temperature requirements during shipping and avoid losses. By selecting the modified starch with a specific average molecular weight to make the modified starch have a higher melting temperature and a shorter coagulation time, a screw extruder can be used for pelleting during preparation, so that the fragrance bead can be quickly molded during extrusion to better encapsulate a spice, thereby making the obtained fragrance bead retain fragrance for a long time and have low fragrance loss.

6 Claims, 2 Drawing Sheets

HIGH-TEMPERATURE-RESISTANT FRAGRANCE BEAD AND PREPARATION METHOD THEREFOR

TECHNICAL FIELD

The present disclosure relates to the technical field of fragrance beads, in particular to a high-temperature-resistant fragrance bead and a preparation method therefor.

BACKGROUND

Fragrance beads have a function of leaving fragrance on clothes or fabrics, and are deeply loved by consumers. Especially in tropical areas, this kind of product that can eliminate body odor and retain fragrance for a long time is in greater demand, making large export volume of the fragrance beads. During exportation, in order to reduce transportation costs, shipping is usually chosen and containers are used for packing. However, the containers are usually made of iron. During long-term shipping, the temperature of the containers is usually more than 50° C., and most of the fragrance beads on the market cannot resistant the temperature more than 50° C. for a long time due to their limited temperature resistance. Therefore, long-term high temperature during shipping causes the beads to dissolve, cool, and coagulate, causing the fragrance beads to be unable to be packaged, or even invalidated after reaching their destination, thereby causing a loss to exporters and customers.

Therefore, the prior art still needs to be improved and developed.

SUMMARY

According to the above-mentioned defects of the prior art, a purpose of the present disclosure is to provide a high-temperature-resistant fragrance bead and a preparation method therefor, aiming to improve the temperature resistance of existing fragrance beads.

In order to achieve the above-mentioned purpose, the technical solutions adopted by the present disclosure are as follows.

A high-temperature-resistant fragrance bead, in which a melting temperature of the fragrance bead is >50° C., the fragrance bead uses modified starch as an encapsulating material, and a weight-average molecular weight of the modified starch is 5,000 to 20,000.

The high-temperature-resistant fragrance bead, in which the weight-average molecular weight of the modified starch is 7,000 to 16,000, and the melting temperature of the fragrance bead is 55 to 110° C.

The high-temperature-resistant fragrance bead, in which the modified starch is plant-rhizome-type starch modified by thermophilic or thermotolerant maltose-transglucosylase.

The high-temperature-resistant fragrance bead, in which the plant-rhizome-type starch is potato starch or tapioca starch.

The high-temperature-resistant fragrance bead, in which a shape of the fragrance bead is a multiangular star-shaped sheet-like particle or a multi-petal flower-shaped sheet-like particle.

The high-temperature-resistant fragrance bead, in which a dissolution duration of the fragrance bead at room temperature is 4 to 10 minutes.

The high-temperature-resistant fragrance bead, in which in parts by weight, raw materials for preparing the fragrance bead include: 20 to 95 parts of the encapsulating material, 0.05 to 50 parts of a spice, 0.01 to 40 parts of water, 0.1 to 10 parts of a release agent, and 0.1 to 10 parts of a molding agent.

The high-temperature-resistant fragrance bead, in which the release agent is glycerin or a polymer of glycerin.

The high-temperature-resistant fragrance bead, in which the molding agent is selected from a combination of one or more of polyoxyethylene stearate, plant-based modified ester quaternary ammonium salt, plant-based modified imidazoline quaternary ammonium salt, plant-based modified amide salt, cationic modified starch, cationic modified cellulose or hemicellulose.

A method for preparing a fragrance bead, used to prepare the above-mentioned high-temperature-resistant fragrance bead, includes following steps:

step S1: taking an encapsulating material and a molding agent, stirring and uniformly mixing, adding a spice, a bacteriostatic agent, and a pigment, stirring and uniformly mixing to obtain a mixed material;

step S2: putting the mixed material into a screw extrusion pelleter, adding water and a release agent at the same time, and using the screw extrusion pelleter to uniformly mix, melt, gelatinize, and ripen the material; and step S3: when the material is transported to an extrusion mold frame, reducing a temperature of the material to be lower than a melting temperature of the encapsulating material, extruding and cutting by a rotating cutter, and after cooling and molding, obtaining a pellet of the high-temperature-resistant fragrance bead.

Beneficial Effects

The present disclosure provides a high-temperature-resistant fragrance bead. By using modified starch with a higher melting temperature as an encapsulating material, a melting temperature of the fragrance bead is increased to meet temperature requirements during shipping and avoid losses. At the same time, by selecting the modified starch with a specific weight-average molecular weight to make the modified starch have a higher melting temperature and a shorter coagulation time, a screw extruder can be used for pelleting during preparation, so that the fragrance bead can be quickly molded during extrusion to better encapsulate a spice, thereby making the obtained fragrance bead retain fragrance for a long time and have low fragrance loss.

The method for preparing the high-temperature-resistant fragrance bead provided in a second aspect of the present disclosure uses the screw extruder to perform mixing, melting, gelatinization, ripening, and extruding for pelleting, which has low energy consumption and can obtain a polygonal star-shaped sheet-like fragrance bead particle having better heat dissipation and dissolution speed.

DETAILED DESCRIPTION OF THE EMBODIMENTS

Figure 1:
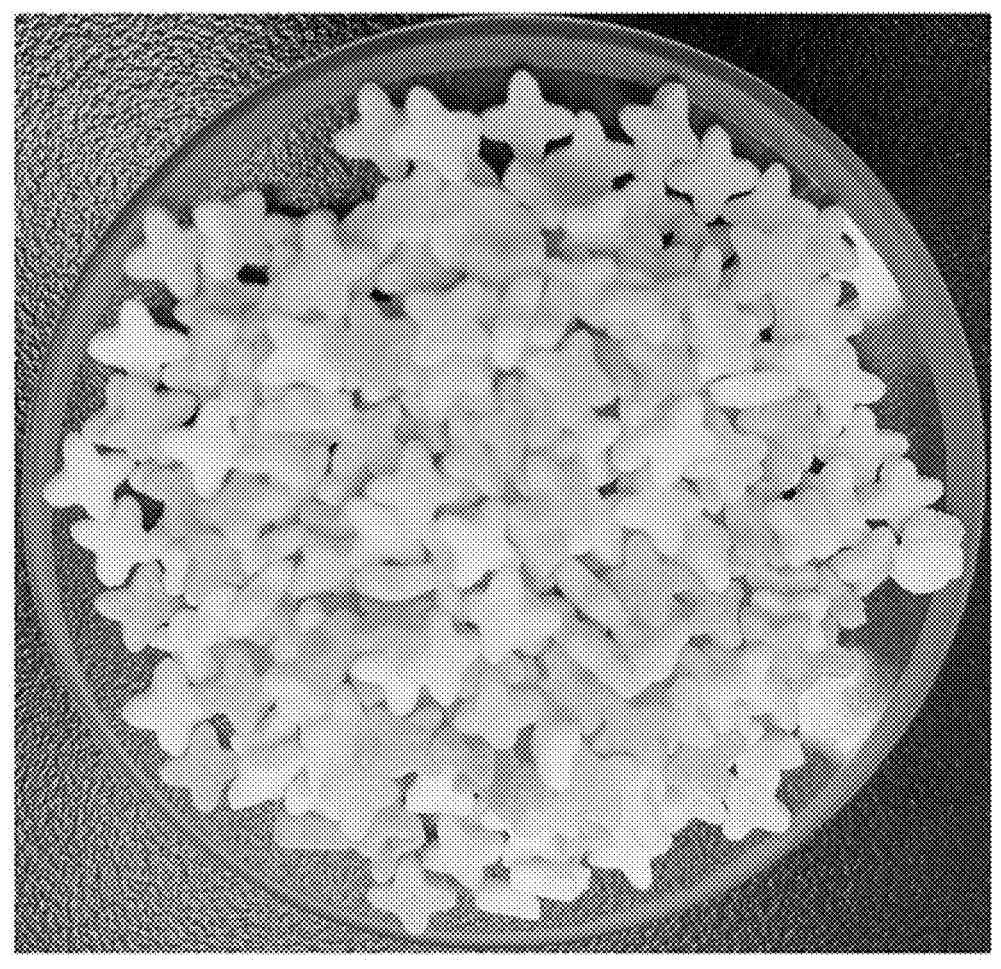
FIG. 1 is a physical diagram of a high-temperature-resistant fragrance bead with a four-pointed star shape provided by the present disclosure.
Figure 2:
FIG. 2 is a physical diagram of a high-temperature-resistant fragrance bead with a flower shape provided by the present disclosure.

The present disclosure provides a high-temperature-resistant fragrance bead and a preparation method therefor. In order to make the purposes, technical solutions, and effects of the present disclosure clearer and more explicit, the following embodiments are given to further describe the present disclosure in detail. It should be understood that the specific embodiments described here are only used to explain the present disclosure and are not intended to limit the present disclosure.

Based on the problem that pellets of existing fragrance beads are repeatedly melted and coagulated due to high temperature during export transportation, which leads to the product to be invalidated and unable to be packaged, a first aspect of the present disclosure provides a high-temperature-resistant fragrance bead. The fragrance bead uses modified starch with a weight-average molecular weight of 5,000-20,000 as an encapsulating material, which can make a melting temperature of the fragrance bead >50° C., and make the fragrance bead resistant a high temperature of 50 to 120° C., so that the fragrance bead has good temperature resistance which can meet requirements during shipping. Even if the fragrance bead is exposed to high temperature and sunlight for a long time, it is not melted and coagulated, so that the fragrance bead can maintain its initial shape and performance.

For the above-mentioned high-temperature-resistant fragrance bead, by adjusting the encapsulating material and selecting the modified starch with a higher melting temperature as the encapsulating material, the melting temperature of the fragrance bead is increased to meet temperature requirements during shipping and avoid losses. At the same time, by selecting the modified starch with a specific weight-average molecular weight, the fragrance bead has a higher melting temperature and a shorter coagulation duration (10 to 360 seconds), so that the fragrance bead can be quickly molded during extrusion, so as to better encapsulate a spice, making the obtained fragrance bead to retain fragrance for a long time and reduce fragrance losses. In addition, the modified starch is a green and environmentally-friendly material, its microbial degradation half-life is <28 days, ammonia nitrogen produced during a degradation process is ≤5 mg/L, a concentration of the ammonia nitrogen is lower than national comprehensive emission level-one standard (15 mg/L) of China and is environmentally friendly.

A type of the modified starch directly affects the melting temperature, viscosity during melting, coagulation duration, and encapsulation performance for other ingredients of the fragrance bead. Generally speaking, starch includes amylose and amylopectin. The higher the content of the amylopectin in plant-rhizome-type starch, the higher the melting temperature. The fragrance bead prepared by the plant-rhizome-type starch has better high-temperature resistance and is difficult to melt and coagulate during shipping. At the same time, the higher the content of the amylopectin, the faster the coagulation, which can reduce losses of flavor during pelleting. At the same time, it is easier to mold the fragrance bead and can obtain a bead particle with a target shape. Therefore, in one preferred embodiment, the modified starch uses the plant-rhizome-type starch as the encapsulating material, such as potato starch or tapioca starch, both of which have high amylopectin content, high melting temperature, and short coagulation duration.

In order to further increase the content of the amylopectin, in one preferred embodiment, the modified starch is plant-rhizome-type starch modified by thermophilic or thermotolerant maltose-transglucosylase. A modification effect of the thermophilic or thermotolerant maltose-transglucosylase can increase the content of the amylopectin in the plant-rhizome-type starch, thereby increasing the melting temperature of the plant-rhizome-type starch and reducing the coagulationduration of the plant-rhizome-type starch. At the same time, through the modification effect of the thermophilic or thermotolerant maltose-transglucosylase, the viscosity of starch can be reduced when the starch is gelatinized and the transparency of the strach can be improved, so as to facilitate the extrusion for pelleting of the fragrance bead. In addition, through the modification of the thermophilic or thermotolerant maltose-transglucosylase, the plant-rhizome-type starch can have better encapsulation performance and can better encapsulate the spice and other active ingredients to make them retain fragrance for a long time.

In addition, since the weight-average molecular weight of the modified starch affects the melting temperature and coagulation duration of the modified starch, the greater the weight-average molecular weight, the higher the melting temperature and the better resistant to ambient temperature, and at the same time, the coagulation duration is shorter and the modified starch is molded quickly which facilitate pelleting during preparation, and at the same time, the spice is better encapsulated. However, when the melting temperature of the modified starch is too high, a gelatinization temperature during preparation is too high, which not only consumes a lot of energy, but also easily results in a loss of the flavor and flavor microcapsules. In one preferred embodiment, the weight-average molecular weight of the modified starch is 5,000 to 20,000. The fragrance bead prepared using the modified starch has a melting temperature of 50 to 120° C. and a coagulation duration of 10 to 360 seconds, with good high-temperature resistance and a small loss of the flavor and flavor microcapsules.

Preferably, the weight-average molecular weight of the modified starch is 7,000 to 16,000. The fragrance bead prepared using the modified starch has a melting temperature of 55 to 110° C. and a coagulation duration of 10 to 180 seconds, with better high-temperature resistance and a smaller loss of the flavor and flavor microcapsules.

More preferably, the weight-average molecular weight of the modified starch is 8,000 to 14,000. The fragrance bead prepared using the modified starch has a melting temperature of 55 to 80° C. and a coagulation duration of 10 to 120 seconds, with more better high-temperature resistant and no loss of the flavor and flavor microcapsules.

In order to further improve the high-temperature resistant of the fragrance bead, besides using the modified starch as the encapsulation material, changing a particle shape of the fragrance bead is also used to expand a specific surface area of the fragrance bead to improve heat dissipation performance of the fragrance bead, so as to reduce the temperature of the bead. In one preferred embodiment, the shape of the fragrance bead is a regular sheet-shaped particle such as multiangular star shape, multi-petal flower shape, etc. Since the multiangular star shape has multiple edges-and-corners and the multi-petal flower shape has multiple petals, these edges-and-corners or the petals can greatly expand the specific surface area of the bead, which is more conducive to the heat dissipation, thereby improving the temperature resistance of the fragrance bead, so that the fragrance bead can remain an intact particle without melting under an ambient temperature above 50° C. for a long time, and has better viewing effect and is more popular among consumers.

In addition, the fragrance bead particle with a polygonal star shape such as the multiangular star shape, multi-petal flower shape, etc. can better contact with water and expand contact area with the water. Therefore, a dissolution duration can be greatly reduced during use. For example, under a normal-temperature condition, the dissolution duration of spherical and hemispherical fragrance beads in the water is 20 to 30 minutes, while the dissolution duration of the multiangular star-shaped and multi-petal flower-shaped fragrance beads with the same diameter as the spherical and hemispherical fragrance beads is only 4 to 10 minutes, which is greatly shortened, thereby it can meet requirements of washing machine's fast-washing mode and has better adaptability.

However, it requires a very short coagulation duration during preparing the fragrance bead with a polygonal star-shaped sheet-like structure. Especially during extrusion molding, due to that a distance from an extrusion opening to a conveyor belt is limited, after the material is extruded through an extruder, the material is cut into pellets by a rotating cutter, so as to avoid deformation or bonding when the pellets fall into the conveyor belt. Thus, the material is quickly cooled and molded when it falls, therefore the coagulation duration of the encapsulating material is required to be very short, and a preparation device is required to have a corresponding cooling mechanism to ensure quick cooling and molding of the pellets.

In one preferred embodiment, in parts by weight, raw materials for preparing the fragrance bead include: 20 to 95 parts of an encapsulating material, 0.05 to 50 parts of a spice, and 0.01 to 40 parts of water. Moreover, the encapsulating material is the aforementioned modified starch, which has the characteristics of high melting temperature, fast coagulation duration, and good encapsulation effect; the spice includes flavour and a flavour capsule, which have the effect of flavoring clothes; the water has a moistening effect, and during preparation, the modified starch can be moistened by the effect of the water, thereby facilitating gelatinization and ripening of the modified starch. In addition, in order to make the fragrance bead have the effect of sterilization and disinfection, 0.001 to 10 parts of a bacteriostatic agent may be further added. In order to make the fragrance bead have a better appearance and color, 0.0001 to 10 parts of a pigment may be further added, so as to better attract consumers.

Since the material is required to be quickly molded after extrusion during preparation, the present disclosure reduces the coagulation duration of the material so that the pellets can be quickly cooled and molded when they fall. In addition, in one preferred embodiment, a molding agent is added to improve the molding effect of the material. For example, 0.1 to 10 parts of the molding agent are added to the raw materials for preparing the fragrance bead. The molding agent is selected from a combination of one or more of polyoxyethylene stearate, plant-based modified ester quaternary ammonium salt, plant-based modified imidazoline quaternary ammonium salt, plant-based modified amide salt, cationic modified starch, cationic modified cellulose or hemicellulose, which can quickly cool and mold the molten material during extrusion and achieve a better molding effect. The polyoxyethylene stearate, plant-based modified ester quaternary ammonium salt, plant-based modified imidazoline quaternary ammonium salt, plant-based modified amide salt, cationic modified starch, cationic modified cellulose or hemicellulose were purchased from Nanfeng County Daxin Technology Co., Ltd.

In addition, due to relatively high viscosity of the modified starch during gelatinization and ripening, the modified starch is easy to stick to an extrusion device, causing extrusion pressure to increase and extrusion temperature to rise. Firstly it leads to material loss, and secondly it is prone to excessive ripening leading to carbonization, thereby making it impossible to produce qualified products. In one preferred embodiment, 0.1 to 10 parts of a release agent is further added to the raw materials for preparing the fragrance bead. The release agent may be glycerol or a polymer of glycerol. During the extrusion process of a screw extruder, the release agent precipitates to an outer surface of the material and adheres to an inner wall of the screw extruder, which can prevent the modified starch from adhering to the inner wall and achieve a lubrication effect, thereby not only facilitating demoulding, but also reducing the extrusion pressure and the extrusion temperature during extrusion, so that qulified products can be prepared.

In summary, the high-temperature-resistant fragrance bead of the present disclosure can greatly improve the high-temperature resistance of the finished fragrance bead by using the modified starch with high molecular weight as the encapsulating material, thereby meeting the requirement of high-temperature conditions during shipping; at the same time, by controlling the molecular weight of the modified starch, the modified starch has a shorter coagulation duration, thereby achieving quick cooling and molding during preparation, so that the loss of flavor and flavor microcapsules is small, the fragrance-enhancing and fragrance-retaining effects are better, and the molding effect is good.

A second aspect of the present disclosure provides a method for preparing a fragrance bead, which is used to prepare the above-mentioned high-temperature-resistant fragrance bead. The preparation method uses a screw extrusion pelleter for pelleting. The method includes the following steps:

Step S1: Taking an encapsulating material and a molding agent, stirring and uniformly mixing; then adding a spice, a bacteriostatic agent, and a pigment, stirring and uniformly mixing to obtain a mixed material;

Step S2: Putting the mixed material into the screw extrusion pelleter, and adding water and a release agent at the same time; through an action of both screw extrusion and a heating mechanism, the material is mixed uniformly, melted, gelatinized, and ripened during a transport process; during a screw-extrusion process, an internal temperature of a screw is controlled to be 3 to 5° C. higher than a ripening temperature of the encapsulating material, and a specific temperature is set according to a type and a molecular weight of the encapsulating material; and Step S3: when the material is melted, mixed uniformly, and transported to an extrusion mold frame, a temperature of a module is controlled to be slightly lower than a melting temperature of the encapsulating material, the material is extruded and cut into pellets by a rotating cutter, and after cooling and molding, a high-temperature-resistant fragrance bead with a polygonal star-shaped structure is obtained.

It should be noted that when the device is initially used, a certain amount of the release agent can be put into the screw extruder first to wet the device to achieve a better release effect.

In the present embodiment, the raw materials for preparing the fragrance bead can be mixed uniformly, melted, gelatinized, and ripened through the screw extrusion pelleter, and in the present process, the spice and the bacteriostatic agent are encapsulated in the encapsulating material, thereby having the characteristics of fast mixing rate and low energy consumption. At the same time, by controlling a temperature of a screw-extrusion end, the material is mixed uniformly and ripened without carbonization. By controlling a temperature of the extrusion mold frame, the material can be quickly coagulated and molded after extrusion, so that the fragrance bead with a specific shape can be prepared.

To further illustrate the high-temperature-resistant fragrance bead and the preparation method therefor provided by the present disclosure, following embodiments are provided.

Example 1

A high-temperature-resistant fragrance bead is provided, the fragrance bead is a five-pointed star-shaped sheet-like particle. In parts by weight, raw materials for preparing the fragrance bead include: 75 parts of modified starch (weight-average molecular weight is 10,000), 3 parts of a release agent, 6 parts of a molding agent, 45 parts of a spice, 6 parts of a bacteriostatic agent, 2 parts of a pigment, 30 parts of water.

The method for preparing the fragrance bead includes following steps:

Step S1: Taking an encapsulating material and the molding agent, stirring and uniformly mixing; then adding the spice, the bacteriostatic agent, and the pigment, stirring and uniformly mixing to obtain a mixed material;

Step S2: Putting the mixed material into a screw extrusion pelleter, and adding the water and the release agent at the same time; through an action of both screw extrusion and a heating mechanism, the material was mixed uniformly, melted, gelatinized, and ripened during a transport process; during a screw-extrusion process, an internal temperature of a screw was controlled to be 3° C. higher than a ripening temperature of the encapsulating material, and a specific temperature was set according to a type and a molecular weight of the encapsulating material; and Step S3: when the material was transported to an extrusion mold frame, a temperature of the material was reduced to be 1 to 3° C. lower than a melting temperature of the encapsulating material, the material was extruded and cut by a rotating cutter, and after cooling and molding, a high-temperature-resistant fragrance bead with a polygonal star-shaped structure was obtained.

Example 2

A high-temperature-resistant fragrance bead is provided, the fragrance bead is a five-pointed star-shaped sheet-like particle. In parts by weight, raw materials for preparing the fragrance bead include: 20 parts of modified starch (weight-average molecular weight is 20,000), 0.1 parts of a release agent, 0.1 parts of a molding agent, 50 parts of a spice, 10 parts of a bacteriostatic agent, 1 part of a pigment, 0.01 parts of water.

Example 3

A high-temperature-resistant fragrance bead is provided, the fragrance bead is a five-pointed star-shaped sheet-like particle. In parts by weight, raw materials for preparing the fragrance bead include: 95 parts of modified starch (weight-average molecular weight is 5,000), 10 parts of a release agent, 10 parts of a molding agent, 0.05 parts of a spice, 0.001 parts of a bacteriostatic agent, 1 part of a pigment, 40 parts of water.

Example 4

A high-temperature-resistant fragrance bead is provided, the fragrance bead is a five-pointed star-shaped sheet-like particle. In parts by weight, raw materials for preparing the fragrance bead include: 50 parts of modified starch (weight-average molecular weight is 8,000), 5 parts of a release agent, 5 parts of a molding agent, 40 parts of a spice, 10 parts of a bacteriostatic agent, 1 part of a pigment, 10 parts of water.

Example 5

A high-temperature-resistant fragrance bead is provided, the fragrance bead is a five-pointed star-shaped sheet-like particle. In parts by weight, raw materials for preparing the fragrance bead include: 60 parts of modified starch (weight-average molecular weight is 7,000), 7 parts of a release agent, 7 parts of a molding agent, 30 parts of a spice, 8 parts of a bacteriostatic agent, 1 part of a pigment, 20 parts of water.

Example 6

A high-temperature-resistant fragrance bead is provided, the fragrance bead is a five-pointed star-shaped sheet-like particle. In parts by weight, raw materials for preparing the fragrance bead include: 70 parts of modified starch (weight-average molecular weight is 16,000), 8 parts of a release agent, 4 parts of a molding agent, 20 parts of a spice, 4 parts of a bacteriostatic agent, 1 part of a pigment, 30 parts of water.

It should be noted that the preparation methods of Examples 2 to 6 are basically the same as the preparation method of Example 1, and the modified starch in Examples 1 to 6 is potato starch or tapioca starch both modified by thermophilic or thermotolerant maltose-transglucosylase; the release agent in Examples 1-6 may be glycerol or a polymer of glycerin; the molding agent is selected from a combination of one or more of polyoxyethylene stearate, plant-based modified ester quaternary ammonium salt, plant-based modified imidazoline quaternary ammonium salt, plant-based modified amide salt, cationic modified starch, cationic modified cellulose or hemicellulose.

Comparative Example 1

A fragrance bead is provided, the fragrance bead is a hemispherical shape. In parts by weight, raw materials for preparing the fragrance bead include: 75 parts of polyethylene glycol (weight-average molecular weight is 10,000), 3 parts of a release agent, 6 parts of a molding agent, 45 parts of a spice, 6 parts of a bacteriostatic agent, and 1 part of a pigment.

Comparative Example 2

A fragrance bead is provided, the fragrance bead is a five-pointed star-shape sheet-like particle. In parts by weight, raw materials for preparing the fragrance bead include: 75 parts of modified starch (weight-average molecular weight is 2,000), 3 parts of a release agent, 6 parts of a molding agent, 45 parts of a spice, 6 parts of a bacteriostatic agent, 1 part of a pigment, and 30 parts of water.

Comparative Example 3

A fragrance bead is provided, the fragrance bead is a five-pointed star-shape sheet-like particle. In parts by weight, raw materials for preparing the fragrance bead include: 75 parts of modified starch (weight-average molecular weight is 10,000), 6 parts of a molding agent, 45 parts of a spice, 6 parts of a bacteriostatic agent, 1 part of a pigment, and 30 parts of water.

Comparative Example 4

A fragrance bead is provided, the fragrance bead is a five-pointed star-shape sheet-like particle. In parts by weight, raw materials for preparing the fragrance bead include: 75 parts of modified starch (weight-average molecular weight is 10,000), 3 parts of a release agent, 45 parts of a spice, 6 parts of a bacteriostatic agent, 1 part of a pigment, and 30 parts of water.

Comparative Example 5

A fragrance bead is provided, the fragrance bead is a five-pointed star-shape sheet-like particle. In parts by weight, raw materials for preparing the fragrance bead include: 75 parts of potato starch (weight-average molecular weight is 10,000, without being modified by the thermophilic or thermotolerant maltose-transglucosylase), 3 parts of a release agent, 45 parts of a spice, 6 parts of a bacteriostatic agent, 2 parts of a pigment, and 30 parts of water.

It should be noted that the preparation methods of Comparative Examples 1 to 5 was basically the same as the preparation method of Example 1.

Performance Testing

Melting temperature, dissolution duration, and high-temperature resistance of Examples 1-6 and Comparative Examples 1-5 were tested. The melting temperature was measured using a microscopic melting-point instrument (model number: SGWR X-4B); the dissolution duration: at room temperature, adding 100 mL pure water into a glass beaker with a volume of 300 mL, extending a stirring paddle into a middle position of a surface of the water, adjusting a rotation speed of a mechanical stirring device (model number: GZ120-S) to 250±2 rad/min, accurately weighing 1.0 g fragrance-bead sample with an average particle size of 5 mm, then adding into the beaker and starting a stopwatch at the same time until the sample was completely dissolved in the water, and recording the required duration; the high-temperature resistance: after the fragrance bead particle was placed in an oven (model number: LRH-70F) for 2 hours at a temperature of 50° C., the temperature was cooled to room temperature in a dryer, then the temperature was raised to 50° C. lasting for 2 hours, this cycle was repeated 10 times to observe whether the particle was melted and coagulated. Specific testing results are shown in Table 1.

TABLE 1

| | Performance Testing Results | | |
|---|---|---|---|
| | Melting temperature/° C. | Dissolution duration/min | High-temperature resistance |
| Example 1 | 75 | 6 | No melting |
| Example 2 | 115 | 10 | or coagulation |
| Example 3 | 55 | 4 | phenomenon occurred |
| Example 4 | 64 | 7.5 | |
| Example 5 | 58 | 7 | |
| Example 6 | 110 | 8 | |
| Comparative Example 1 | 48 | 9 | Melting occurred and coagulated |
| Comparative Example 2 | 45 | 2 | Melting occurred and coagulated |
| Comparative | 74 | 5 | No melting |

TABLE 1-continued

| | Performance Testing Results | | |
|---|---|---|---|
| | Melting temperature/° C. | Dissolution duration/min | High-temperature resistance |
| Example 3 | | | phenomenon occurred |
| Comparative Example 4 | 68 | 4.5 | No melting phenomenon occurred |
| Comparative Example 5 | 47 | 4.2 | Melting occurred and coagulated |

It can be seen from Table 1 that the high-temperature-resistant fragrance beads of Examples 1 to 6 all have a relatively high melting temperature, are not melted under a high-temperature condition of 50° C., and have good high-temperature resistance. At the same time, the dissolution durations of Examples 1 to 6 are very short. Comparative Example 1 uses polyethylene glycol as the encapsulating material, and its melting temperature is lower than 50° C., therefore, a melting phenomenon occurs during the high-temperature-resistance experiment. Comparative Example 2 uses the modified starch that has relatively small weight-average molecular weight, so that its melting temperature is relatively low, resulting in poor high-temperature resistance. The melting temperature of Comparative Example 3 is relatively high, but since no release agent is added, the temperature during extrusion is relatively high, the carbonization occurs, thereby making the produced fragrance bead show a yellowing phenomenon, leading to poor appearance and reducing fragrance-retaining effect. Since no molding agent is added in Comparative Example 4, its molding effect is poor, making it difficult to produce a star-shaped or flower-shaped sheet-like particle, thus making its heat-dissipation effect worse than that of Example 1. Comparative Example 5 uses unmodified potato starch as the encapsulating material, thus its melting temperature is reduced and its high-temperature resistance is poor.

It is understood that those ordinary skilled in the art can make equivalent substitutions or changes based on the technical solutions and inventive concepts of the present disclosure, and all these changes or substitutions should fall within the protection scope of the appended claims of the present disclosure.

What is claimed is:

1. A fragrance bead for fabric care applications, comprising: 20 to 95 parts by weight of a modified starch as an encapsulating material and 0.1 to 10 parts by weight of a molding agent, wherein a melting temperature of the fragrance bead is >greater than 50° C. and an average molecular weight of the modified starch is 5,000 to 20,000, and wherein the modified starch is plant rhizome starch modified by thermophilic or thermotolerant maltose-transglucosylase; wherein the molding agent is selected from the group consisting of plant-based modified ester quaternary ammonium salt, plant-based modified imidazoline quaternary ammonium salt, and plant-based modified amide salt; a shape of the fragrance bead is a multiangular star-shaped particle or a multi-petal flower-shaped particle; and a dissolution duration of the fragrance bead at room temperature is 4 to 10 minutes.

2. The fragrance bead according to claim 1, wherein the average molecular weight of the modified starch is 7,000 to 16,000, and the melting temperature of the fragrance bead is 55° C. to 110° C.

3. The fragrance bead according to claim 1, wherein the plant rhizome starch is potato starch or tapioca starch.

4. The fragrance bead according to claim 1, wherein, in parts by weight, raw materials for preparing the fragrance bead further include: 0.05 to 50 parts of a spice, 0.01 to 40 parts of water, and 0.1 to 10 parts of a release agent.

5. The fragrance bead according to claim 4, wherein the release agent is glycerin or a polymer of glycerin.

6. A method for preparing a fragrance bead according to claim 1, the method comprising:

i) stirring and uniformly mixing 20 to 95 parts by weight of a modified starch as an encapsulating material with 0.1 to 10 parts by weight of a molding agent, and then adding a spice, a bacteriostatic agent, and a pigment with stirring and uniformly mixing to obtain a mixed material;

ii) adding the mixed material into a screw extrusion pelleter, and then adding water and a released agent at the same time into the screw extrusion pelleter, followed by uniformly mixing, melting, gelatinizing, and ripening to form a uniformly mixed, melted, gelatinized, and ripened material;

iii) transporting the uniformly mixed, melted, gelatinized, and ripened material to an extrusion mold frame, followed by reducing a temperature of the uniformly mixed, melted, gelatinized, and ripened material to be lower than a melting temperature of the encapsulating material, and then extruding and cutting by a rotating cutter the uniformly mixed, melted, gelatinized, and ripened material; and iv) cooling and molding the uniformly mixed, melted, gelatinized, and ripened material to form the fragrance bead into a multiangular star-shaped particle or a multi-petal flower-shaped particle, wherein a melting temperature of the fragrance bead is greater than 50° C. and an average molecular weight of the modified starch is 5,000 to 20,000, wherein the modified starch is plant rhizome starch modified by thermophilic or thermotolerant maltose-trans-glucosylase, wherein the molding agent is selected from the group consisting of plant-based modified ester quaternary ammonium salt, plant-based modified imidazoline quaternary ammonium salt, and plant-based modified amide salt, and wherein a dissolution duration of the fragrance bead at room temperature is 4 to 10 minutes.

\* \* \* \* \*